United States Patent [19]

Mentelos

[11] 4,301,807
[45] Nov. 24, 1981

[54] APPARATUS AND METHOD FOR TEMPERATURE COMPENSATED TRANSCUTANEOUS CARBON DIOXIDE MEASUREMENT

[75] Inventor: Richard A. Mentelos, Hamden, Conn.

[73] Assignee: Novametrix Medical Systems, Inc., Wallingford, Conn.

[21] Appl. No.: 100,501

[22] Filed: Dec. 5, 1979

[51] Int. Cl.³ .............................................. A61B 5/00
[52] U.S. Cl. ................................ 128/635; 204/195 B; 204/195 P
[58] Field of Search .............................. 128/635, 632; 204/195 B, 195 P, 195 R; 324/441

[56] References Cited

U.S. PATENT DOCUMENTS

| | | | |
|---|---|---|---|
| Re. 30,317 | 7/1980 | Lubbers et al. | 128/635 |
| 3,000,805 | 9/1961 | Carritt et al. | 128/635 X |
| 3,432,418 | 3/1969 | Kleiss | 204/195 P |
| 3,528,904 | 9/1970 | Cliffgard | 204/195 P |
| 3,710,778 | 1/1973 | Cornelius | 204/195 B X |
| 3,909,386 | 9/1975 | Oswin et al. | 204/195 R |
| 4,197,853 | 4/1980 | Parker | 128/635 |

OTHER PUBLICATIONS

Bergveld, "Electronic Circuit Design Principles . . . ", Mod & Biol. Eng. & Comput., 1979, 17, 655-661.
Brown et al., "Oxygen Transport to Tissue", Pharmacology, Mat. Studies & Neonatology, pp. 1103-1108, 1973.

*Primary Examiner*—Lee S. Cohen
*Attorney, Agent, or Firm*—Howard F. Mandelbaum

[57] ABSTRACT

An improved apparatus for non-invasive measurement of transcutaneous carbon dioxide pressure employs a skin engaging sensor including pH and reference electrodes and a temperature sensor. The temperature sensor produces an output signal voltage having a characteristic which can be the same as or the complement of the voltage-temperature characteristic of the deviation voltage component of the pH-reference electrode voltage attributable to temperature deviation effects on the sensor as well as on the skin. An error signal voltage produced at the output of the temperature sensor is combined with the voltage measured across the pH and reference electrodes to provide a corrected voltage having a magnitude indicative of transcutaneous carbon dioxide pressure at a predetermined reference temperature without need to heat the skin or electrode or otherwise control their temperatures.

18 Claims, 2 Drawing Figures

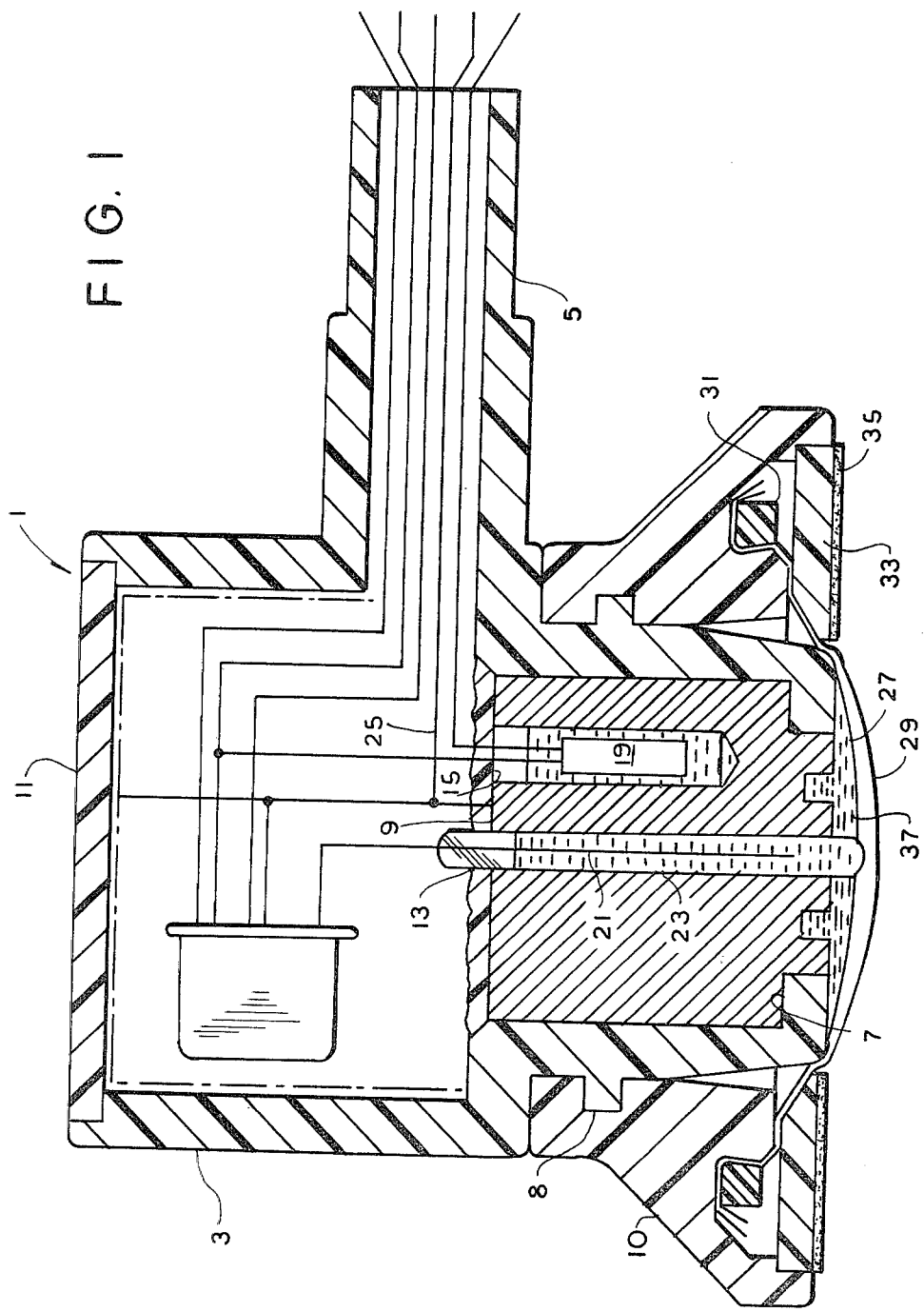

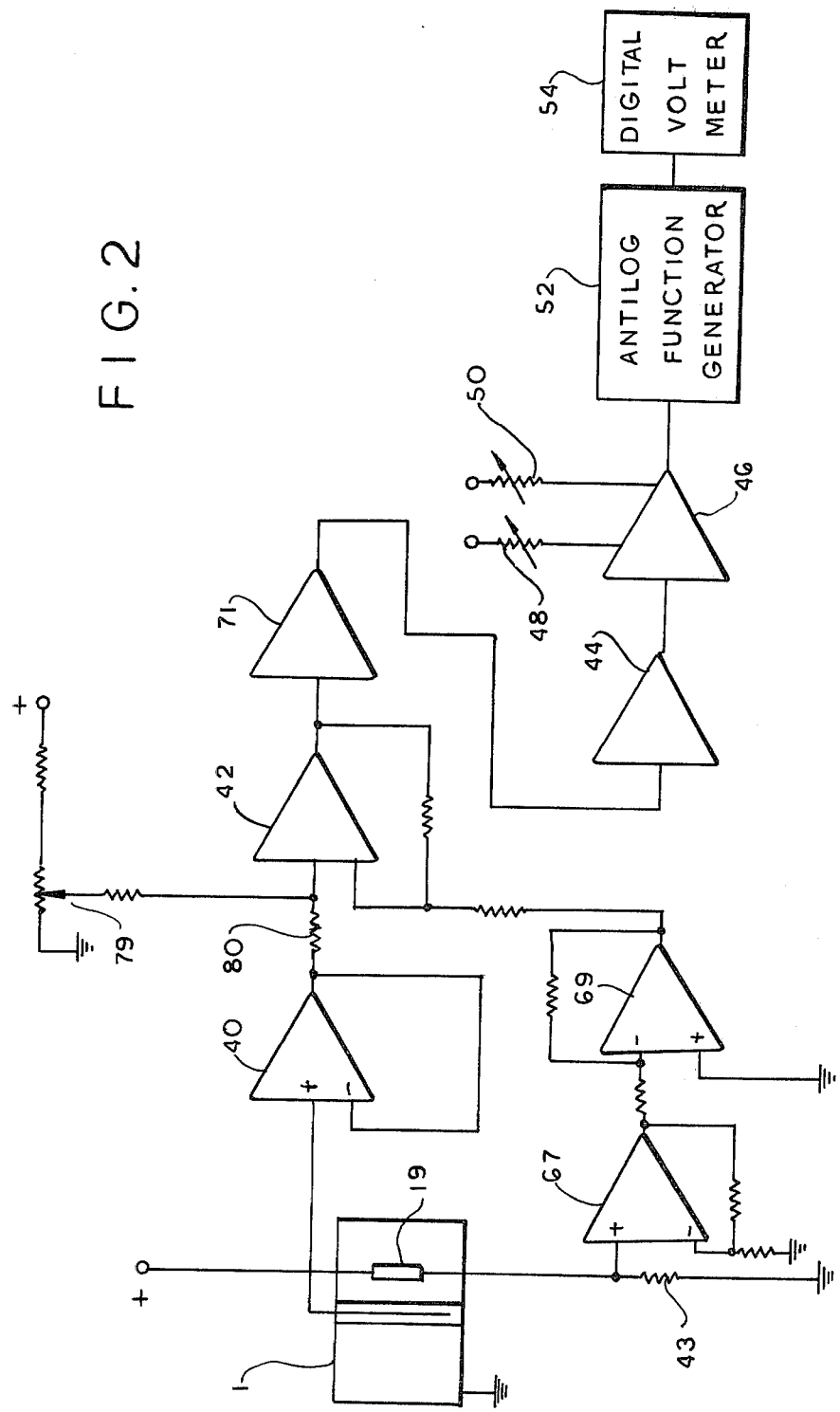

APPARATUS AND METHOD FOR TEMPERATURE COMPENSATED TRANSCUTANEOUS CARBON DIOXIDE MEASUREMENT

BACKGROUND OF THE INVENTION

The present invention relates to the field of transcutaneous gas measuring apparatus for non-invasive measurement of blood gases which are transcutaneous through the skin of a living body. More specifically, the invention concerns an apparatus and method for determining the amount of a gas which is transcutaneous through the skin at a predetermined reference temperature while permitting variations in temperature from the reference temperature during the measurement and, hence, without need to heat or otherwise control the temperature of the skin or measuring apparatus during the measurement.

It is known in the medical art of non-invasive blood gas content monitoring and measurement to apply to the surface of the skin of the person whose blood gas content is to be monitored and measured, a probe having a barrier permeable to the gas to be measured. The gas to be measured is permitted to diffuse through the barrier which is normally a membrane having specific diffusion properties and into a solution stored above the membrane in which the gas is soluble. An electrode assembly in contact with the solution is used to measure the effect of the dissolved gas on the electrical properties of the solution to provide a quantitative indication of the amount of gas emitted from the skin.

In the case of transcutaneous carbon dioxide measurement, a sensor is used to measure the pressure of the carbon dioxide transcutaneous through the skin at a region of the skin to which the membrane assembly of the electrode is applied. The anode, which is referred to as the reference electrode, and cathode, which is referred to as the pH electrode of the transcutaneous carbon dioxide sensor, are in contact with an electrolytic solution in which the carbon dioxide transcutaneous through the permeable membrane is dissolved. As a result of the dissolving of the carbon dioxide in the electrolytic solution, a voltage is induced between the reference and pH electrodes which is proportional to the logarithm of the transcutaneous carbon dioxide pressure or tension at the skin surface. Hence, the induced voltage can be processed by suitable circuitry and then displayed on a volt meter to give a direct reading of transcutaneous carbon dioxide pressure or tension.

It is known in the art of medicine that transcutaneous carbon dioxide pressure varies significantly with changes in temperature. In order to make useful diagnoses of a patient's condition based on transcutaneous carbon dioxide pressure, it has been found necessary to obtain all transcutaneous carbon dioxide pressure readings at a standard predetermined reference temperature and to compare such measurements with standards of what are normal and abnormal transcutaneous carbon dioxide pressures developed for the same reference temperature.

Prior art transcutaneous carbon dioxide measurement devices have dealt with the problem of temperature variation during transcutaneous carbon dioxide measurements by employing means to stabilize the temperatures of the skin and engaging measurement apparatus. Some transcutaneous blood gas measuring systems employ probes which include electrical heaters that are thermostatically controlled to maintain the probe and adjacent skin temperatures as close as possible to the reference level. U.S. Pat. No. 3,659,586 to Johns et al for a Percutaneous Carbon Dioxide Sensor and Process for Measuring Pulmonary Efficiency discloses a transcutaneous carbon dioxide measuring probe which includes a lead baseplate to serve as a thermal sink for minimizing temperature changes.

The approaches taken in the prior art to prevent temperature variations are only partially effective as constantly changing environmental conditions as well as metabolic conditions of the patient continuously cause temperature variations and fluctuations all of which degrade the accuracy of transcutaneous carbon dioxide pressure measurements. Moreover, the necessity for adding temperature stabilization devices to the gas measuring probes, such as heaters and thermal sinks, increases the cost and complexity of the probes, and can result in discomfort to the patient.

SUMMARY OF THE INVENTION

The present invention overcomes the aforementioned problems of prior art transcutaneous carbon dioxide pressure measuring devices in providing a transcutaneous carbon dioxide pressure measuring apparatus and method which permits probe and skin temperatures to vary from a predetermined reference temperature, measures the temperature variation and compensates the transcutaneous carbon dioxide pressure reading of the measuring system to compensate for the measured temperature variation. Specifically, the present invention is directed to apparatus for correcting the output signal of a transcutaneous carbon dioxide pressure measurement probe to compensate for deviations in the output signal due to temperature variations including temperature sensor means for sensing the temperature of the probe and providing an output signal having a characteristic with a magnitude proportional to the probe temperature and an error signal generating circuit including a function generating circuit which employs a function which has a characteristic the same as or the complement of the probe output voltage-temperature characteristic, and having an input adapted to receive the temperature signal from the temperature sensor means and an output at which an error signal is provided as a function of the measured temperature, and means for combining the error signal with the probe output signal to offset the deviation in the magnitude of the probe output signal attributable to temperature variations thereby providing a signal having a characteristic with a magnitude indicative of transcutaneous carbon dioxide pressure at the predetermined reference temperature.

It is therefore an object of the invention to provide an apparatus and method for measuring transcutaneous carbon dioxide pressure at the skin surface of a patient at a predetermined reference temperature irrespective of deviations in actual temperature from the reference temperature.

Another object of the invention is to provide for the measurement of transcutaneous carbon dioxide pressure without need to stabilize the temperature of the measuring probe or skin surface to which the probe is applied.

Still another object of the present invention is to provide for the measurement of transcutaneous carbon dioxide pressure at the skin surface of a patient extrapolated to a predetermined reference temperature which can be different from the actual temperature at the time of measurement.

A further object of the invention is to provide an apparatus and a method for developing an error signal having a characteristic the same as or complementary to the characteristic of transcutaneous carbon dioxide pressure measurement signals attributable to deviations from a predetermined reference temperature for offsetting the deviation portion of such pressure measurement signals.

Other and further objects of the invention will be apparent from the following drawings and description of a preferred embodiment of the invention in which like reference numerals are used to indicate like parts in the various views.

DESCRIPTION OF THE DRAWINGS

FIG. 1 is a sectional elevation view of a transcutaneous carbon dioxide measuring probe used with the apparatus and method of the preferred embodiment of the invention.

FIG. 2 is a schematic block diagram illustrating the circuitry of the transcutaneous carbon dioxide pressure measurement apparatus of the preferred embodiment of the invention.

DESCRIPTION OF THE PREFERRED EMBODIMENT

Referring now to FIG. 1 of the drawings, there is shown a transcutaneous carbon dioxide probe 1 according to the invention. The probe includes a housing formed from an irregularly shaped cylindrical shell 3, having a vertical axis in the view of FIG. 1, and further having an integrally molded lateral extension 5 with a cylindrical bore having a horizontal axis in the view of FIG. 1.

The shell 3 has a radially inwardly directed bottom defining a circular shoulder 7 in the interior of its bore. The shell 3 is provided on its exterior with threads 8 adapted to mate with a removable fixation ring 10 having complementary threads on its exterior.

Mounted within the shell 3 is a substantially cylindrical mass 9 of a conductive metal which in the preferred embodiment of the invention is silver. Silver is chosen as a result of its superior electrical and heat conducting properties but other conductors, e.g., copper, having similar properties, can be employed with acceptable results. The silver mass 9 serves as the reference electrode for the probe 1 and has a constant outer diameter for the major portion of its length and a smaller diameter portion at one end thereby forming a circular shoulder to mate with the shoulder 7 of the shell 3 so that silver mass 9 can be supported within the shell 3 with its lowermost surface in the view of FIG. 1 substantially in the same plane as the lowermost surface of the shell 3. A circular cover member 11 is fitted on top of the shell 3 after insertion of the silver mass 9. The cover 11 may be welded in place or firmly secured by use of a known adhesive or a forced fit or a combination of the foregoing.

The cylindrical silver mass 9 as an axial bore 13 throughout its length, with an axis common to the axes of the cylindrical mass 9 and the shell 3. In addition, there is another axial bore 15 having an axis parallel to and radially displaced from the common axis of the central bore 13, cylindrical silver mass 9 and shell 3. The bore 15 partially penetrates the depth of the cylindrical mass 9, as can clearly be seen in FIG. 1. The bore 15 is partially filled with a thermal compound in which there is supported a temperature sensor 19 which includes a field effect transistor which when energized provides an output voltage having a magnitude proportional to the temperatures of the electrolyte solution and the silver reference electrode 9, as the temperature sensor 19 is in intimate thermal contact with the silver reference electrode 9. A pair of leads extends from the temperature sensor 19 for applying the temperature indicating voltage output of the sensor 19 to electrical circuitry which will be subsequently described with reference to FIG. 2.

A silver wire 21 coated with a layer of silver chloride is disposed on the axis of the central bore 13 and is suspended in an electrolytic solution containing a mixture of sodium bicarbonate and sodium chloride to provide chloride ions. The electrolytic solution is contained within a glass tube 23 which is snuggly received in the bore 13 within the silver reference electrode 9. The end of the wire 21 opposite the end disposed in the electrolytic solution is connected to a cable which extends from the probe through the horizontal bore in the lateral section 5 of the shell 3. The wire 21, glass tube 23 and the electrolyte solution therein, form the pH electrode of the sensor 1. A wire 25 is connected to the mass 9 and is also extended through the horizontal bore in the lateral section 5 of the shell 3.

The fixation ring 10 has stretched across its circular opening a barrier including an upper membrane 27 and a lower membrane 29. The membranes 27 and 29 are held in place by a single O-ring or snap ring 31. A circular cover ring 33 also supports the membranes 27 and 29 on the fixation ring 10. The cover ring 33 can be provided with a layer of an adhesive material 35 on its lowermost surface to insure adherence of the probe to the skin of the person whose carbon dioxide blood content is being measured or monitored. In use, the membranes 27 and 29 are tightly stretched over the bottom of the reference electrode 9 and the pH electrode 23. The membranes are shown somewhat separated in the drawing of FIG. 1 for ease of understanding their disposition on the probe.

The upper membrane 27 is absorbent and acts as a spacer between the lower membrane 29 and an electrolytic solution 37, disposed between the upper surface of the membrane 27 and the lower surface of the reference electrode silver mass 9. The upper membrane 27 is preferably made from a cellulose material which wil absorb the electrolyte and the lower membrane 29 is made of a carbon dioxide permeable material which in the preferred embodiment of the invention is teflon. The electrolyte 37 can be the same sodium bicarbonate sodium chloride solution used within the glass envelope 23 of the pH electrode.

Referring now to FIG. 2 of the drawings, there is shown a schematic diagram of an electrical circuit used to measure and monitor blood carbon dioxide content with the aid of the probe illustrated in FIG. 1. The pH electrode of the probe 1 is connected to the positive input of a unity gain amplifier 40 having a feedback loop from its output to its inverting input. The resultant signal at the output of the amplifier 40 is a voltage having a magnitude proportional to the logarithm of the transcutaneous carbon dioxide pressure or tension measured at the region of probe contact with the skin surface. The voltage output of the amplifier 40 is applied through a resistor 80 to one input of an amplifier 42 which can be a differential amplifier or a summing amplifier depending on the selected circuit design as will subsequently be explained.

The temperature sensor 19 which includes a temperature dependent field effect transistor (FET) energized by a power supply (not shown), provides a current output having a magnitude proportional to the temperature of the sensor which, due to the high conductivity of the silver reference electrode, is continuously maintained within one tenth of one degree centrigrade of the temperature of the pH electrode. A signal derived from the current output of the temperature sensor 19 is developed and applied to the other input of the amplifier 42 to provide at the corresponding input of the amplifier 42 a voltage having a magnitude proportional to the temperature of the sensor 19.

The current output of the temperature sensor element 19 is applied to a resistor 43 to develop a voltage having a magnitude proportional to the temperature. In the preferred embodiment of the invention, the resistor 43 has a nominal value of 10,000 ohms. The voltage across resistor 43 is applied to an amplifier 67, the output of which is connected to a feedback amplifier 69 where the correct amount of feedback is applied for compensation to restore the signal to its proper level.

The compensated output of amplifier 69 is then applied to the other input of the amplifier 42 where the signals having voltages with magnitudes respectively proportional to carbon dioxide tension and sensor temperature are combined. The carbon dioxide signal voltage input to the amplifier 42 is connected to the wiper of a potentiometer 79 which is connected to a source of positive voltage for nulling the output of the transcutaneous carbon dioxide probe 1.

When the temperature of the probe deviates from the nominal temperature to which measurements are to be normalized, the temperature input signal is combined with the carbon dioxide signal in the amplifier 42 so as to offset the change in the carbon dioxide voltage due to temperature effect on the probe and on the patient. The temperature sensor 19 and associated circuitry, including resistor 43, amplifiers 67 and 69, and potentiometer 79 act as a function generator to provide an output voltage dependent on the sensed temperature according to a function which is the same as the voltage versus temperature characteristic of the voltage deviation by which the output voltage of the amplifier 40 at a given temperature deviates from the voltage which would be present at the predetermined reference temperature to which measurements are to be normalized. The FET can be selected to have the desired current versus temperature characteristic or separate function generator circuitry, known to the art, can be used to convert the FET current output to a signal with a current or voltage magnitude which varies with the temperature of the FET according to the desired voltage-temperature characteristic.

The deviation voltage is due to variations in the pH electrode temperature from the reference temperature. Ideally, measurements are made at a pH electrode reference temperature of approximately 35 degrees centrigrade. The inner body temperature of the patient will normally be approximately 37 degrees centigrade and a two degree temperature drop can be expected at the interface of the skin surface and pH electrode due to typical ambient environmental conditions.

The output voltage of the probe 1 as measured at the output of the amplifier 40, has been found to be susceptible to two phenomenon which occur upon temperature variation from the reference temperature. The first source of voltage error is attributable to the temperature coefficient of the electrode which has been found to be on the order to $-1.2$ millivolts per degree centigrade. The voltage deviation resulting from changes in the electrical characteristics of the electrode caused by temperature fluctuations is substantially negatively linear over a temperature range encompassing 35 degrees centrigrade.

A second source of voltage error at the output of amplifier 40 has been found to be attributable to variations in the transcutaneous carbon dioxide pressure or tension at the skin surface which occur with temperature changes. It has been found that when the skin temperature deviates from the reference temperature, the resulting temperature gradient across the skin increases the carbon dioxide pressure at about 2% per degree centigrade. The latter phenomenon is herein referred to as carbon dioxide pressure-skin temperature gradient coefficient effect and causes voltage to vary positively and linearly with skin temperature gradient, that is, with the absolute value of the difference between the skin and reference temperatures. The negative change in voltage at the output of the amplifier 40 due to temperature-voltage coefficient effect is greater than the positive change in voltage due to the carbon dioxide pressure-skin temperature gradient coefficient effect. As a result, the net change in voltage at the output of amplifier 40 due to changes in temperature is inverse with respect to temperature. That is, as temperature increases, the output voltage decreases and as temperature decreases, the output voltage increases. Hence, the characteristic of the deviation voltage, that is, the difference between the output voltage actually measured at the output of amplifier 40 and the voltage which would be measured under conditions where the skin surface and pH electrode were at the reference temperature, is a linear function of temperature having a negative slope. A complementary error signal function having a positive slope equal in magnitude to the magnitude of the negative slope of the deviation voltage can be developed such that when the complementary or error signal function is combined with the deviation voltage function, the net result is zero. That is, the complementary error signal function voltage cancels the deviation voltage. Whether the error signal has a characteristic the same as or the complement of the deviation voltage depends on whether the signals at the inputs of the amplifier 42 are added together or subtracted, one from the other. The magnitude of the error signal voltage is substantially equal to the magnitude of the deviation voltage portion of the voltage at the output of the amplifier 42 at every temperature within the expected range of temperature deviation from 35 degrees centrigrade. The sign of the error signal voltage is the same as the sign of the deviation voltage portion if the amplifier 42 is a differential amplifier. If the amplifier 42 is a summing amplifier, then the complementary error signal having a slope with a sign opposite to that of the deviation voltage slope is used.

Hence, the temperature sensor 19 and its output processing circuitry are designed to yield an output voltage versus temperature characteristic which is the same as or the complement of the deviation voltage characteristic due to the voltage-temperature coefficient effect combined with the carbon dioxide pressure-skin temperature gradient coefficient effect. In the preferred embodiment of the invention, the FET included in the temperature sensor 19 gives an output of 1 microampere per degree centigrade. The output voltage of the amplifier 40 is summed with the error signal voltage output of the temperature sensor 19, when the error signal voltage is the complement of the deviation voltage portion of the amplifier 40 output voltage, in the amplifier 42 if it is a summing amplifier so that the voltage at the output of the summing amplifier 42 has a magnitude indicative of the voltage output of the probe 1 which would obtain in the absence of temperature variation from the reference temperature. If the amplifier 42 is a differential amplifier, the function generator of the temperature sensor 19 is selected to provide a voltage output variable with temperature which has the same characteristic as the deviation voltage versus temperature characteristic instead of the complement.

The temperature compensated output signal of amplifier 42 is applied to the input of a high gain amplifier 71 which in the preferred embodiment of the invention has a gain of 50. The increased gain allows use of less sensitive signal measurement circuitry than would otherwise be required. For patient safety, the output of the high gain amplifier 71 is applied to the input of an isolation amplifier 44 having unity gain and a very high input impedance. The isolation amplifier 44 prevents any dangerous voltage condition existing at the output of the amplifier 44 from effecting the probe 1 which is attached to the skin of the patient.

The output of the isolation amplifier 44 is connected to the input of a calibration amplifier 46 which includes a first potentiometer control 48 for adjusting the voltage output of the amplifier 46 so that when the probe 1 is in an environment of 5% carbon dioxide, the voltage output of the amplifier 46 has a magnitude of $-0.1$ v. A second potentiometer control 50 is used to adjust the range of the output voltage of the amplifier 46 so that after the low adjustment has been made, the probe can be placed in an environment of 10% carbon dioxide pressure or tension and the amplifier 46 adjusted to provide an output voltage with a magnitude porportional to the logarithm of the known carbon dioxide pressure, that is, $-0.085$ in the preferred embodiment of the invention.

The output of the amplifier 46 is applied to the input of an antilog function generator 52. The output of the function generator circuit 52 is a voltage having a magnitude equal to the antilog of the magnitude of the input voltage applied to the function generator 52. Hence, the magnitude of the output voltage of the antilog function generator 52 is numerically equal to the transcutaneous carbon dioxide pressure sought to be measured.

The output of the antilog function generator 52 is applied to the input of a digital volt meter 54 which displays in digital form the converted transcutaneous carbon dioxide pressure measurement on a seven segment display employing light emitting diodes, liquid crystals or similar devices.

The amplifiers 40, 67, 69, 42, 71, 44 and 46, the antilog function generator 52 and the digital volt meter 54 are all known elements which are commercially available as will be known to those skilled in the art of electronic circuit design.

Instead of using a digital volt meter 54 to display the transcutaneous carbon dioxide measurement, other known display devices can be used, including chart recorders and alphanumeric printers.

It is to be appreciated that the foregoing description is of a preferred embodiment of the invention which may be altered or modified without departing from the spirit and scope of the invention which is defined in the following claims.

What is claimed is:

1. A transcutaneous carbon dioxide probe for producing a signal having a characteristic with a magnitude indicative of carbon dioxide perfusion through the skin substantially independent of temperature variations comprising pH sensitive electrode means having a surface adapted to engage the skin and an output terminal at which there is produced an output signal having a characteristic with a magnitude which varies with the magnitude of carbon dioxide emitted through the skin at the region of engagement, temperature sensor means for sensing the temperature of said pH electrode means and generating an error signal independent of said output signal and having a characteristic with a magnitude dependent on the temperature of said pH electrode means, and means for combining said output signal and said error signal to produce a corrected signal having a characteristic with a magitude indicative of transcutaneous carbon dioxide pressure at a predetermined temperature.

2. Apparatus according to claim 1 wherein said temperature sensor means includes a temperature sensitive element having an output at which there is produced a current having a magnitude proportional to temperature.

3. Apparatus according to claim 2 further comprising means for maintaining the voltage-temperature function of said temperature sensor means substantially linear over a temperature range including 35 degrees centigrade.

4. Apparatus according to claim 3 further comprising means for maintaining the slope of said voltage-temperature function in predetermined relationship to the voltage-temperature coefficient of said probe.

5. Apparatus according to either of claims 3 and 4 further comprising means for maintaining the slope of the voltage-temperature function of said probe at a magnitude dependent upon the carbon dioxide pressure-skin temperature gradient coefficient.

6. A transcutaneous carbon dioxide sensor comprising a pH electrode, a reference electrode, a carbon dioxide dissolving solution in contact with said electrodes and means for engaging the skin surface of a person whose carbon dioxide pressure output is to be measured, said engaging means maintaining said solution in contact with said electrodes and being permeable to carbon dioxide to permit the carbon dioxide to be measured to be dissolved in said solution, measuring circuit means responsive to the voltage induced across said pH and reference electrodes in response to the carbon dioxide dissolved in said solution for producing an output signal having a characteristic with a magnitude indicative of the pressure of carbon dioxide transcutaneous through the skin, compensating means responsive to the temperature of said sensor for providing an error signal independent of said output signal and having a characteristic with a magnitude dependent on said temperature, and combining means operatively connected to said measuring circuit means and to said compensating means and responsive to said error signal and said output signal for producing a corrected signal having a characteristic with a magnitude indicative of transcutaneous carbon dioxide pressure at a predetermined temperature.

7. Apparatus according to claim 6 wherein said compensating means comprises temperature sensitive means for producing a temperature current having a characteristic with a magnitude variable with temperature, said error signal being dependent on said temperature current.

8. Apparatus according to claim 6 wherein said compensating means comprises a temperature sensitive device providing a signal variable with temperature and error signal generating circuit means responsive to said temperature sensitive device for generating said error signal in response to temperature.

9. Apparatus according to claim 8 further comprising means for maintaining the magnitude of said error signal as a function of the magnitude of a characteristic of said temperature sensitive device signal.

10. Apparatus according to claim 9 further comprising means for maintaining said function substantially linear over a temperature range including thirty-five degrees centigrade.

11. Apparatus for measuring transcutaneous carbon dioxide comprising a sensor including a pH electrode, a reference electrode, a carbon dioxide dissolving solution in contact with said pH and reference electrodes, said solution generating a voltage across said electrodes when carbon dioxide is dissolved therein and means for engaging the skin surface of a person whose carbon dioxide output is to be sensed, said engaging means having one surface in contact with said solution, said engaging means being permeable to carbon dioxide to permit the carbon dioxide to be sensed to be dissolved in said solution, temperature signal generating means mounted in said sensor and responsive to the temperature of said sensor for producing an error signal independent of the voltage across said reference and pH electrodes having a characteristic with a magnitude dependent upon said temperature, and means for combining said error signal with the voltage across said reference and pH electrodes, said combining means having an output at which there is produced a voltage having a characteristic with a magnitude indicative of transcutaneous carbon dioxide pressure at said skin surface.

12. Apparatus according to claim 11 wherein said temperature signal generating means includes a temperature sensor having an output voltage with a voltage temperature characteristic which is the same as the voltage-temperature characteristic of the deviation voltage equal to the difference between the voltage across the pH and reference electrodes at a predetermined referenced temperature and the voltage across said electrodes at the temperature of said sensor.

13. Apparatus according to claim 11 wherein said temperature signal generating means includes a temperature sensor having an output voltage with a voltage temperature characteristic which is the complement of the voltage-temperature characteristic of the deviation voltage equal to the difference between the voltage across the pH and reference electrodes at a predetermined referenced temperature and the voltage across said electrodes at the temperature of said sensor.

14. A method of correcting the output signal of a transcutaneous carbon dioxide measuring apparatus having a skin engaging probe and means for generating said output signal in response to transcutaneous carbon dioxide gas pressure sensed by said probe to correct for deviations in temperature from a predetermined reference temperature comprising measuring the temperature of said probe, generating an error signal independent of said output signal having a characteristic with a magnitude dependent on said temperature, and combining said error signal with said output signal to yield a corrected signal.

15. A method according to claim 14 further comprising causing said error signal characteristic to have a voltage-temperature relationship related to that of the voltage-temperature characteristic of said probe.

16. A method according to claim 15 wherein said error signal characteristic voltage-temperature relationship is related to the voltage-temperature characteristic of said probe and the carbon dioxide pressure-skin temperature gradient characteristic.

17. A method according to claim 14 further comprising causing said error signal characteristic to have a voltage-temperature relationship complementary to the voltage-temperature characteristic of said probe.

18. A method according to claim 14 further comprising causing said error signal characteristic to have a voltage-temperature relationship complementary to a function which combines the voltage-temperature characteristic of said probe and the carbon dioxide pressure-skin temperature gradient coefficient effect characteristic.

* * * * *